US009463089B2

(12) United States Patent
Brown et al.

(10) Patent No.: US 9,463,089 B2
(45) Date of Patent: Oct. 11, 2016

(54) PLUNGER SYSTEM FOR INTRAOCULAR LENS SURGERY

(75) Inventors: Kyle Brown, Fort Worth, TX (US); David Anthony Downer, Fort Worth, TX (US)

(73) Assignee: NOVARTIS AG, Basel (CH)

( * ) Notice: Subject to any disclaimer, the term of this patent is extended or adjusted under 35 U.S.C. 154(b) by 83 days.

(21) Appl. No.: 13/476,556

(22) Filed: May 21, 2012

(65) Prior Publication Data

US 2013/0310843 A1 Nov. 21, 2013

(51) Int. Cl.
*A61F 2/16* (2006.01)

(52) U.S. Cl.
CPC .............. *A61F 2/167* (2013.01); *A61F 2/1678* (2013.01)

(58) Field of Classification Search
CPC ..... A61F 2/1662; A61F 2/1667; A61F 2/167
USPC ......................................... 623/6.12; 606/107
See application file for complete search history.

(56) References Cited

U.S. PATENT DOCUMENTS

| | | | |
|---|---|---|---|
| 4,681,102 A | 7/1987 | Bartell | |
| 4,765,329 A | 8/1988 | Cumming et al. | |
| 4,852,566 A | 8/1989 | Callahan et al. | |
| 5,195,526 A | 3/1993 | Michelson | |
| 5,275,604 A | 1/1994 | Rheinish et al. | |
| 5,425,734 A | 6/1995 | Blake | |
| 5,494,484 A | 2/1996 | Feingold | |
| 5,499,987 A | 3/1996 | Feingold | |
| 5,571,113 A | 11/1996 | McDonald | |
| 5,616,148 A | 4/1997 | Eagles et al. | |
| 5,620,450 A | 4/1997 | Eagles et al. | |
| 5,653,715 A | 8/1997 | Reich et al. | |
| 5,716,364 A | 2/1998 | Makker et al. | |
| 5,772,666 A * | 6/1998 | Feingold et al. | ............. 606/107 |
| 5,800,442 A | 9/1998 | Wolf et al. | |
| 5,810,834 A | 9/1998 | Heyman | |
| 5,873,879 A | 2/1999 | Figueroa et al. | |

(Continued)

FOREIGN PATENT DOCUMENTS

| | | |
|---|---|---|
| CN | 1536979 | 10/2004 |
| CN | 201022790 | 2/2008 |

(Continued)

OTHER PUBLICATIONS

International Search Report and Written Opinion for PCT/US2013/41992, 6 pages, dated Aug. 13, 2013.
Supplementary European Search Report and Annex to the European Search Report issued for EP Application No. 13794376 dated Feb. 26, 2015, 7 pgs.
English translation of Chinese Office Action issued for CN 201380020196.4 dated Jul. 27, 2015, 9 pgs.

(Continued)

*Primary Examiner* — Katherine M Shi
*Assistant Examiner* — Michael Mendoza
(74) *Attorney, Agent, or Firm* — Haynes and Boone, LLP

(57) ABSTRACT

Various systems, apparatuses, and processes may be used for intraocular lens surgery. In particular implementations, a system for intraocular lens surgery may include a shell, a plunger, and a deformable sleeve. The shell may, for example, include an outer wall and an inner wall, wherein the inner wall defines a passage through the body. The plunger may be adapted to move within the passage and include first end adapted to be engaged by a user for advancing the plunger within the passage and a second end adapted to interface with an intraocular lens. The deformable sleeve may be sized to fit around the plunger and adapted to engage with the shell and the plunger to provide force feedback to advancing the plunger through the passage.

20 Claims, 4 Drawing Sheets

(56) References Cited

U.S. PATENT DOCUMENTS

| | | |
|---|---|---|
| 5,876,406 A | 3/1999 | Wolf et al. |
| 5,876,440 A | 3/1999 | Feingold |
| 5,928,245 A | 7/1999 | Wolf et al. |
| 5,942,277 A | 8/1999 | Makker et al. |
| 5,944,725 A | 8/1999 | Cicenas et al. |
| 5,947,976 A | 9/1999 | Van Noy et al. |
| 6,001,107 A | 12/1999 | Feingold |
| 6,010,510 A | 1/2000 | Brown et al. |
| 6,048,348 A | 4/2000 | Chambers et al. |
| 6,059,791 A | 5/2000 | Chambers |
| 6,074,397 A | 6/2000 | Chambers et al. |
| 6,083,230 A | 7/2000 | Makker et al. |
| 6,162,229 A | 12/2000 | Feingold et al. |
| 6,241,737 B1 | 6/2001 | Feingold |
| 6,283,975 B1 | 9/2001 | Glick et al. |
| 6,312,433 B1 | 11/2001 | Butts et al. |
| 6,334,862 B1 | 1/2002 | Collinson et al. |
| 6,355,046 B2 | 3/2002 | Kikuchi et al. |
| 6,387,101 B1 | 5/2002 | Butts et al. |
| 6,398,788 B1 | 6/2002 | Makker et al. |
| 6,398,789 B1 | 6/2002 | Capetan |
| 6,406,481 B2 | 6/2002 | Feingold et al. |
| 6,447,519 B1 | 9/2002 | Brady et al. |
| 6,447,520 B1 | 9/2002 | Ott et al. |
| 6,468,282 B2 | 10/2002 | Kikuchi et al. |
| 6,471,708 B2 | 10/2002 | Green |
| 6,491,697 B1 | 12/2002 | Clark et al. |
| 6,503,275 B1 | 1/2003 | Cumming |
| 6,506,195 B2 | 1/2003 | Chambers et al. |
| 6,537,283 B2 | 3/2003 | Van Noy |
| 6,607,537 B1 | 8/2003 | Binder |
| 6,679,891 B2 | 1/2004 | Makker et al. |
| 6,723,104 B2 | 4/2004 | Ott |
| 6,733,507 B2 | 5/2004 | McNicholas et al. |
| 6,976,989 B1 | 12/2005 | Vincent |
| 7,014,641 B2 | 3/2006 | Kobayashi et al. |
| 7,037,328 B2 | 5/2006 | Vincent |
| 7,156,854 B2 | 1/2007 | Brown et al. |
| 7,320,690 B2 | 1/2008 | Beavers et al. |
| 7,348,038 B2 | 3/2008 | Makker et al. |
| 7,687,097 B2 | 3/2010 | Makker et al. |
| 7,947,049 B2 | 5/2011 | Vaquero |
| 8,021,423 B2 | 9/2011 | Tanaka |
| 8,080,017 B2 | 12/2011 | Tanaka |
| 8,152,817 B2 | 4/2012 | Tanaka |
| 8,273,122 B2 | 9/2012 | Anderson |
| 8,425,595 B2 | 4/2013 | Tsai et al. |
| 8,439,973 B2 | 5/2013 | Bogaert |
| 8,470,032 B2 | 6/2013 | Inoue et al. |
| 8,545,512 B2 | 10/2013 | Ichinohe et al. |
| 8,685,088 B2 | 4/2014 | Anderson |
| 8,702,795 B2 | 4/2014 | Shoji et al. |
| 8,784,485 B2 | 7/2014 | Tsai et al. |
| 8,920,494 B2 | 12/2014 | Catlin et al. |
| 2002/0151904 A1 | 10/2002 | Feingold et al. |
| 2005/0149057 A1 | 7/2005 | Rathert |
| 2005/0154399 A1 | 7/2005 | Weber et al. |
| 2005/0222578 A1 | 10/2005 | Vaquero |
| 2006/0167466 A1 | 7/2006 | Dusek |
| 2006/0200167 A1 | 9/2006 | Peterson et al. |
| 2006/0229634 A1 | 10/2006 | Shepherd |
| 2006/0235429 A1 | 10/2006 | Lee et al. |
| 2006/0235430 A1 | 10/2006 | Le et al. |
| 2007/0050023 A1 | 3/2007 | Bessiere et al. |
| 2007/0150056 A1 | 6/2007 | Meyer |
| 2007/0270945 A1 | 11/2007 | Kobayashi et al. |
| 2008/0200921 A1 | 8/2008 | Downer |
| 2008/0312661 A1 | 12/2008 | Downer et al. |
| 2009/0005788 A1 | 1/2009 | Rathert |
| 2009/0018548 A1 | 1/2009 | Charles |
| 2009/0030425 A1 | 1/2009 | Smiley et al. |
| 2009/0054904 A1 | 2/2009 | Holmen |
| 2009/0171366 A1 | 7/2009 | Tanaka |
| 2009/0191087 A1 | 7/2009 | Klein et al. |
| 2009/0240257 A1* | 9/2009 | Meyer .......................... 606/107 |
| 2010/0125278 A1 | 5/2010 | Wagner |
| 2010/0161049 A1 | 6/2010 | Inoue |
| 2010/0312254 A1 | 12/2010 | Downer et al. |
| 2011/0144653 A1 | 6/2011 | Pankin et al. |
| 2012/0221102 A1 | 8/2012 | Tanaka et al. |
| 2013/0060256 A1 | 3/2013 | Han |
| 2013/0226194 A1* | 8/2013 | Wanders et al. ............... 606/107 |
| 2014/0012277 A1 | 1/2014 | Matthews et al. |
| 2014/0200589 A1 | 7/2014 | Anderson |
| 2014/0222013 A1 | 8/2014 | Argal et al. |

FOREIGN PATENT DOCUMENTS

| | | |
|---|---|---|
| CN | 101292913 | 10/2008 |
| CN | 101677857 | 3/2010 |
| CN | 102151194 | 8/2011 |
| EP | 1290990 | 3/2003 |
| EP | 1360944 | 11/2003 |
| EP | 1800622 | 6/2007 |
| EP | 1958594 | 8/2008 |
| EP | 2085053 | 8/2009 |
| JP | 2008-024462 | 8/2009 |
| JP | 2009-183366 | 8/2009 |
| RU | 2138232 | 9/1999 |
| RU | 2242956 | 12/2004 |
| RU | 2261727 | 10/2005 |
| RU | 2294722 | 3/2007 |
| RU | 2379010 | 1/2010 |
| SU | 1440496 | 11/1988 |
| SU | 1706614 | 1/1992 |
| WO | WO 96/37152 | 11/1996 |
| WO | WO9713476 | 4/1997 |
| WO | WO9726844 | 7/1997 |
| WO | WO9801089 | 1/1998 |
| WO | WO9815244 | 4/1998 |
| WO | WO9826733 | 6/1998 |
| WO | WO9837830 | 9/1998 |
| WO | WO9962436 | 12/1999 |
| WO | WO 02/060338 | 8/2002 |
| WO | WO 02 083216 | 10/2002 |
| WO | WO 2007/080868 | 7/2007 |
| WO | WO2007097221 | 8/2007 |
| WO | WO 2007/098622 | 9/2007 |
| WO | WO2007128886 | 11/2007 |
| WO | WO2009002789 | 12/2008 |
| WO | WO2012004592 | 1/2012 |
| WO | WO2013021347 | 2/2013 |
| WO | WO2013035939 | 3/2013 |
| WO | WO2013076067 | 5/2013 |
| WO | WO2013137208 | 9/2013 |
| WO | WO2013184727 | 12/2013 |
| WO | WO2014039353 | 3/2014 |
| WO | WO2014065426 | 5/2014 |
| WO | WO2014074860 | 5/2014 |
| WO | WO2014084355 | 6/2014 |
| WO | WO2014104271 | 7/2014 |

OTHER PUBLICATIONS

International Search Report for PCT/US2010/037374, 3 pages, dated Mar. 9, 2010.

Written Opinion for PCT/US2010/037374, 7 pages, dated Mar. 9, 2010.

International Search Report for PCT/US2009/067814, Publication No. WO2010/080351, dated Apr. 1, 2010, 5 pages.

PCT International Preliminary Report on Patentability, PCT/US2009/067814, dated Jun. 21, 2011, 6 pages.

European Search Report and Opinion, EP EP12160448.2, dated Jun. 25, 2012, 5 pages.

European Search Report for Application No. 08102185.9, Publication No. EP2002803, Published Dec. 17, 2008, dated Apr. 25, 2008, 3 pages.

* cited by examiner

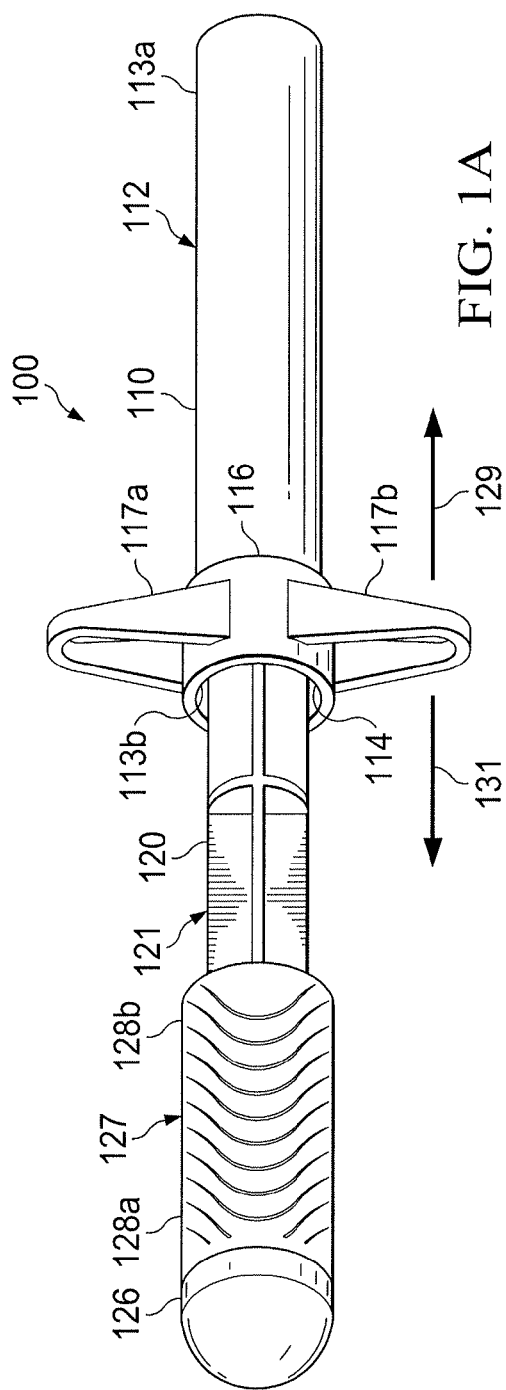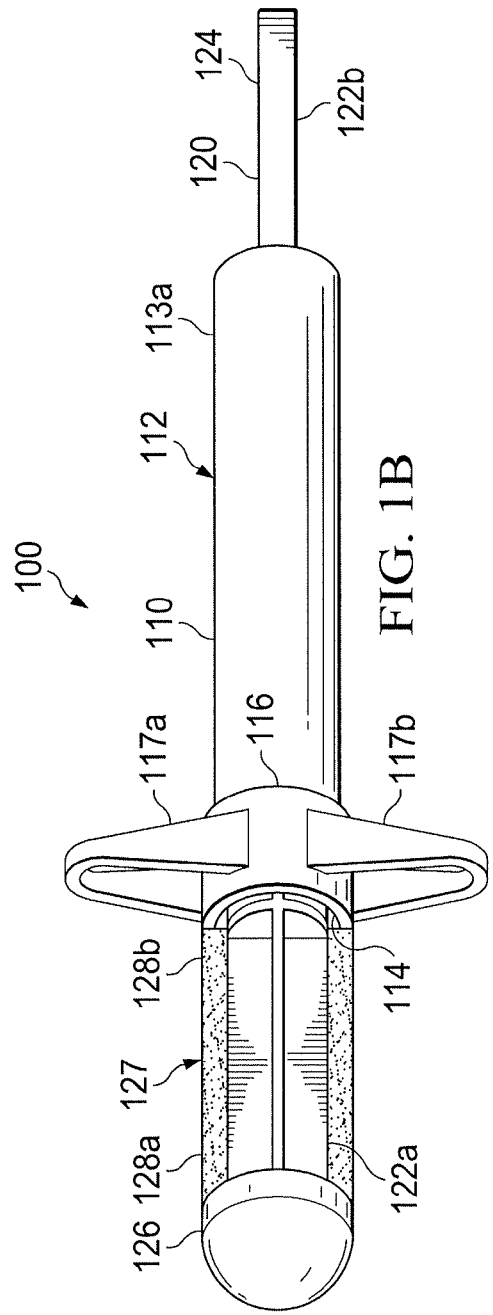
FIG. 1A
FIG. 1B

PLUNGER SYSTEM FOR INTRAOCULAR LENS SURGERY

BACKGROUND

The present disclosure relates to optical surgery, and more specifically to surgical replacement of a patient's lens.

The human eye, in simple terms, functions to provide vision by transmitting and refracting light through a clear outer portion called the cornea and focusing the image by way of the lens onto the retina at the back of the eye. The quality of the focused image depends on many factors including the size, shape, and length of the eye, and the shape and transparency of the cornea and lens.

When trauma, age, or disease causes the lens to become less transparent, vision deteriorates because of a reduction in light transmitted to the retina. This deficiency in the eye's lens is medically known as a cataract. The treatment for this condition is often surgical removal of the lens and implantation of an artificial lens, typically termed an intraocular lens (IOL).

An IOL is often foldable and inserted into the eye through a relatively small incision by being advanced through an IOL insertion cartridge, which causes the IOL to fold. The IOL is typically advanced through the insertion cartridge by a plunger-like device. Unfortunately, as the lens is inserted, the forces that the physician is required to exert on the plunger to move the lens can change drastically (e.g., sudden large decreases) and cause the IOL to suddenly shoot into the eye, which can cause improper IOL placement and damage to eye tissue.

In order to deter uncontrolled plunger advancement rate, some IOL injector systems utilize a metal spring that becomes compressed as the plunger advances. Thus, as the IOL get closer to the injection point into the eye, there is a resistive force from the spring, which can provide a reaction force that opposes force changes from the IOL. Other IOL injector systems may use interference fits between components to influence the rate of plunger advancement.

SUMMARY

In one general implementation, a system for intraocular lens (IOL) surgery may include a shell, a plunger, and a deformable sleeve. The shell may include an outer wall and an inner wall, wherein the inner wall defines a passage through the body. The plunger may be adapted to move within the passage and include a first end adapted to be engaged by a user for advancing the plunger within the passage and a second end including an intraocular lens interface. The deformable sleeve may be sized to fit around the plunger and be adapted to engage with the shell and the plunger to provide force feedback to advancing the plunger through the passage. The deformable sleeve may, for example, be composed of silicone.

In certain implementations, the deformable sleeve is engaged with the plunger and moves therewith while not engaged with the shell. The deformable sleeve may, for example, be adapted to engage with the outer wall of the shell as the plunger is moved through the passage. As another example, the deformable sleeve may be adapted to engage with the inner wall of the shell as the plunger is moved through the passage.

In some implementations, at least a portion of the deformable sleeve is engaged with the shell, and the deformable sleeve engages with the plunger as the plunger is advanced through the passage. The deformable sleeve may, for example, be engaged with the inner wall of the shell.

In particular implementations, the deformable sleeve is adapted to substantially maintain its shape if advancement force on the plunger is lowered. The shape maintained by the deformable sleeve being the shape at the instant the advancement force is decreased.

Some implementations may include an insertion cartridge that includes a portion adapted to fold an intraocular lens as it passes therethrough. The deformable sleeve may be adapted to begin providing force feedback when the intraocular lens is in the folding portion.

Another aspect of the disclosure includes a method including engaging a plunger with an intraocular lens; moving an end of the plunger towards a shell to advance the intraocular lens relative to an intraocular lens insertion cartridge; engaging a deformable sleeve disposed around the plunger with the shell and the plunger, the engaged deformable sleeve providing force feedback to advancement of the plunger relative to the shell; and advancing the IOL relative to the IOL insertion cartridge with the deformable sleeve providing force feedback. The method may also include positioning the intraocular lens in the insertion cartridge. The method may also include injecting the intraocular lens into an eye. Additionally, the method may include decreasing the force applied to move the plunger towards the shell, such that the deformable sleeve substantially maintains its shape so as not to cause the plunger to rebound away from the shell.

Various implementations may include one or more features. For example, a plunger-type insertion system may provide force feedback as an IOL is prepared for insertion into an eye, which may assist in negating sudden changes in resistance of the IOL and uncontrolled plunger advancement. Moreover, the feedback may occur automatically, with no end user actions, which can ease burden on the user. Additionally, in some implementations, a user can reduce the force being applied to the plunger (e.g., to manipulate another instrument) without the plunger rebounding out of the shell.

The details and features of various implementations will be conveyed by the following description, along with the drawings.

BRIEF DESCRIPTION OF THE SEVERAL VIEWS OF THE DRAWINGS

FIG. 1A shows an example plunger system for intraocular lens surgery in a retracted position.

FIG. 1B is a partial cross-sectional view of the example plunger system of FIG. 1A in a retracted position

DETAILED DESCRIPTION

Figure 2A:
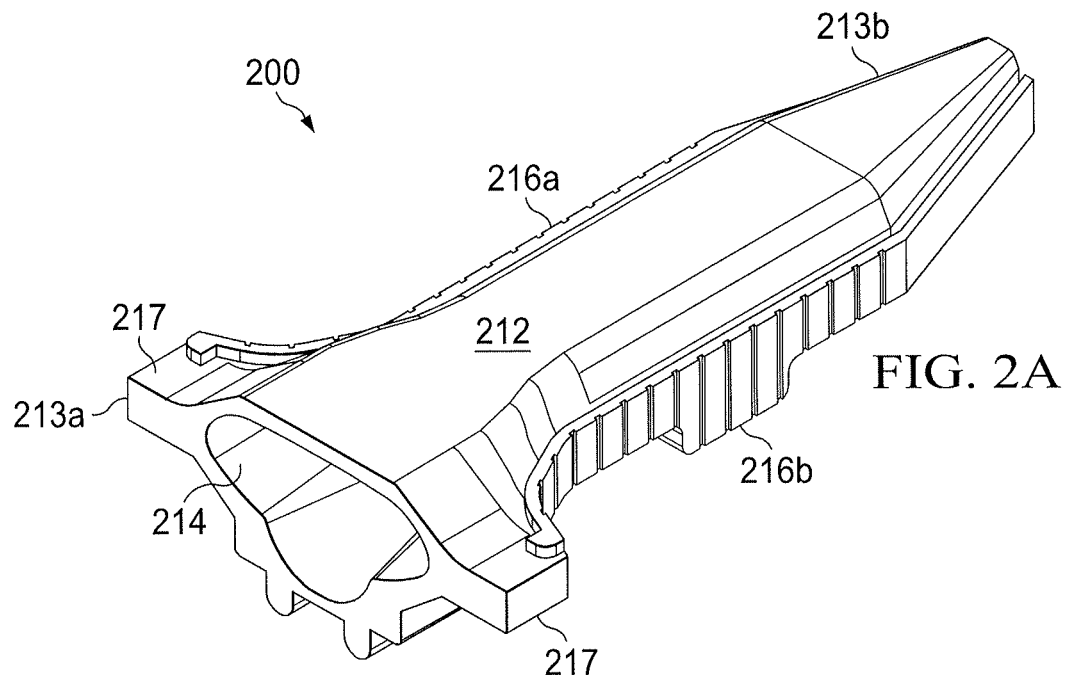
FIGS. 2A-B show an example intraocular lens insertion cartridge.

FIGS. 1A-B illustrate an example plunger system 100 for intraocular lens (IOL) surgery. Plunger system 100 includes a shell 110 and a plunger 120, which is adapted to move within shell 110.

Shell 110 includes a body 112 that has an outer wall 113a and an inner wall 113b, the inner wall defining a passage 114 through the body. As illustrated, body 112 is generally cylindrical in shape, and so is passage 114. In other implementations, body 112 and passage 114 may have cross-sectional shapes other than circular (e.g., oval or any other suitable shape). Shell 110 may also include an annular ring 116 that extends from body 112. Annular ring 116 may include a pair of wings 117a, 117b sized to allow a user (e.g., physician or other medical professional) to manually grasp the wings 117a, 117b (e.g., with a pair of fingers) and, hence, the system 100. Shell 110 may be made of plastic, metal, or any other appropriate material.

Plunger 120 includes a body 121 and has a first end 122a and a second end 122b. As illustrated, first end 122a is sized to fit inside passage 114 while still allowing plunger 120 to move relative thereto. Second end 122b is opposite first end 122a and includes an IOL interface 124. Body 121 may be made of plastic, metal, or any other appropriate material.

IOL interface 124 is operable to interface with an IOL and advance the IOL through an IOL insertion cartridge. IOL interface 124 may, for example, include a body having a first end and a second end. The first end may include a port into which an end of body 121 may be inserted. In the illustrated implementation, IOL interface 124 is rectangular in cross section. However, IOL interface 124 may have other cross-sectional shapes in other implementations. For example IOL interface 124 may have cross-sectional shapes such as oval, ellipsoidal, or any other desired shape. Further, in some implementations, IOL interface 124 may be approximately 2-3 mm in width. IOL interface 124 may be made of an elastomer, such as a commercial injection-molded elastomer; a polymer, such as polypropylene or styrene; metal; or any other appropriate material.

First end 122a may generally taper to the shape of IOL interface 124, or there may be a distinct transition from the shape of first end 122a to the shape of IOL interface 124. In particular implementations, IOL interface 124 may not be integral with plunger 120. For example, IOL interface 124 may be an attachable tip.

Plunger 120 may include an annular ring 126 that extends from body 121 at end 122a. Annular ring 126 may assist a user (e.g., physician or other medical personnel) in manipulating plunger 120 to advance it through shell 110. For example, the annular ring may provide a base at which a digit (e.g., a thumb) may apply force to plunger 120 to advance it through shell 110.

Plunger 120 also includes a sleeve 127 disposed around at least a portion of body 121. The sleeve 127 may be formed from a deformable material 127 that is adapted to decrease the rate at which plunger 120 can advance as end 122b moves through a more resistive portions of a delivery system. For example, a more resistive portion of a delivery system may include a passage having a reduced cross-section. Further, in some implementations, as the plunger 120 is advanced, the sleeve 127 may deform to create resistance to the advancement. The sleeve 127 may prevent uncontrolled advancement of the plunger.

Further, although the illustrated example system 100 includes a sleeve 127 formed from the deformable material, the disclosure is not so limited. Rather, the deformable material may be formed into any suitable shape or form that is operable to provide the resistance to advancement of the plunger 120 through the shell 110, as described below. Therefore, while sleeve 127 is described, other configurations of the deformable material may be used and are within the scope of the disclosure.

The sleeve 127 may include a first end 128a and a second end 128b. The sleeve 127 may be coupled to the body 121, such that the body 121 and the sleeve 127 are moveable together. In operation, as the plunger 120 is moved relative to the shell 110, such that the plunger 120 is moved in the direction of arrow 129, the sleeve 127 engages the shell 110. For instance, the second end 128b of the sleeve 127 may engage an exterior of the shell 110, such as an end surface of the annular ring 116. In other implementations, a portion of the sleeve 127 may be received within the shell 110 between the plunger 120 and the shell 110.

Upon engaging the shell 110, the sleeve 127 may be deformed as the plunger 120 continues to be advanced in the direction of arrow 129 relative to the shell 110. Deformation of the sleeve 127 continues as the end 122a approaches the shell 110. Deformation of the sleeve 127 may occur in any suitable manner. For example, the sleeve 127 may deform by wrinkling, bulging, compressing, and/or any other way. In certain implementations, sleeve 127 may include features to assist in its deformation. For example, in some instances, the sleeve 127 may include cavities, protuberances, grooves, fold lines, etc., to promote deformation thereof.

The deformable material of sleeve 127 may be any suitable material or combination of materials. For example, the deformable material may be dense foam, gel, or silicone. Dense foam may, for example, compress (e.g., due to air being squeezed out of its air pockets) as it is squeezed between plunger 120 and shell 110. Gel or silicone would be reconformed as they are squeezed. The sleeve 127 may generally be adapted to any push-type injection design. Further, in some implementations, the sleeve 127 may have an ergonomic shape.

The sleeve 127 may, for example, be made separately from plunger 120 and then slipped over its body 121. In certain implementations, the sleeve 127 may be overmolded onto the plunger 120. In some instances, one or more portions of the sleeve 127 may be adapted to deform. In other instances, the sleeve 127 may be adapted to deform over its entire length. Further, in some instances, the sleeve 127 may be adapted to deform over a defined range. For example, in some instances, the sleeve 127 may deform over a range of 7-9 mm. In other instances, sleeve 127 may deform over a range up to 15 mm or more. However, these ranges are provided only as examples, and the sleeve 127 may be adapted to deform over any desired range.

Figure 2B:
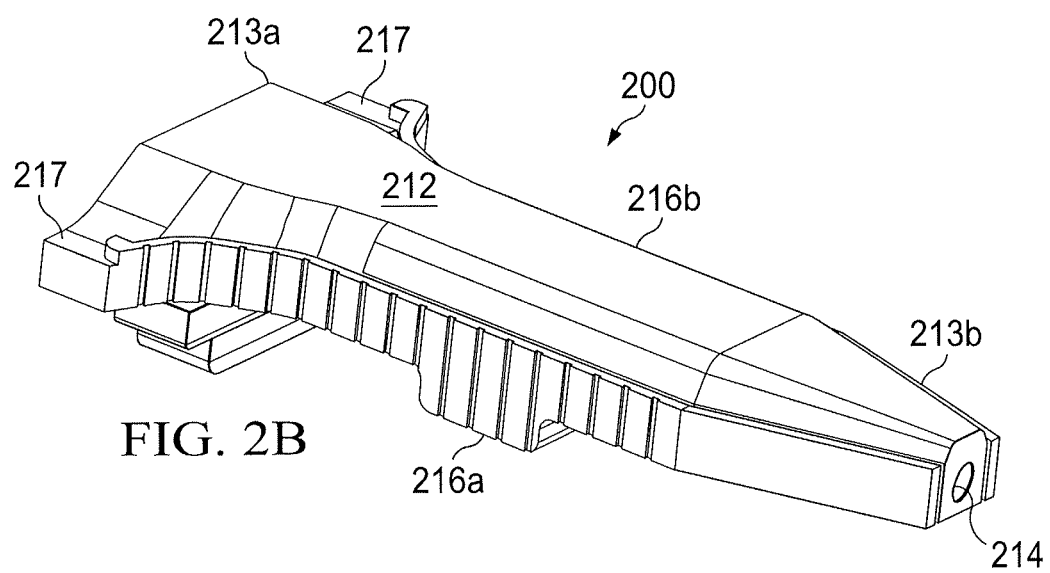

The point at which the sleeve 127 may begin to provide force feedback may be defined. For example, advancement of an IOL through a tip of an IOL insertion cartridge, such as the IOL insertion cartridge shown in FIGS. 2A-2B, is typically when the most force is be applied by the user because of the amount of work needed to conform the IOL to the tip. However, this is often where force changes occur rapidly, because, once the IOL has conformed to the tip of an IOL insertion cartridge, the force feedback from the IOL may drop drastically. Thus, by properly sizing the length of the sleeve 127, deformation of the sleeve 127 may begin to provide force feedback at or near the point where the IOL enters the tip of an IOL insertion cartridge. In other implementations, the length may be adjusted to begin providing force feedback at various other points along the travel of the plunger 120.

In certain modes of operation, end 122a of plunger 120 is retracted from shell 110 at the beginning of use, as shown in FIG. 1A. Then, system 100 is engaged with an IOL insertion cartridge, and plunger 120 is advanced to move IOL interface 124 into the insertion cartridge. IOL interface 124 can then engage an IOL located within the IOL insertion cartridge.

FIGS. 2A-B illustrate an example IOL insertion cartridge 200. IOL insertion cartridge 200 facilitates the insertion of an IOL into a patient's eye. IOL insertion cartridge 200 includes a body 212 that has ends 213a, 213b and a passage 214 through the body. A foldable IOL may be advanced through the passage 214, such as during surgery. The foldable IOL, which may be made of silicone, soft acrylics, hydrogels, or other appropriate materials, may be advanced by the IOL interface 124 through passage 214 in preparation for insertion into the eye. IOL insertion cartridge 200 also includes sides 216a, 216b, which assist in grasping the IOL insertion cartridge 200. Sides 216a, 216b may taper outward to form wings 217a, 217b, which also assist in grasping the IOL insertion cartridge 200.

Passage 214 may have an asymmetric bore at end 213a, which assists in folding an IOL. A common IOL may be approximately 6 mm in diameter, and with haptics can be up to around 13 mm in overall length. However, surgical incisions are typically much smaller (e.g., 2-3 mm in width). An IOL is, therefore, typically folded before insertion through the incision. Passage 214 may also taper along its length to an elliptical bore at end 213b to assist in folding an IOL. Thus, as an IOL is advanced through passage 214, the IOL is folded due to the shape of the passage 214. The end of the passage 214 may be the injection point through which the lens is inserted into an eye. Typically, larger forces occur as the IOL nears end 213b of the IOL insertion cartridge 200 due to the IOL being folded substantially therein.

In certain implementations, IOL insertion cartridge 200 may be molded as a single piece from any suitable thermoplastic. For example, in some instances, the IOL insertion cartridge 200 may be formed from polypropylene. However, the disclosure is not so limited, and the IOL insertion cartridge may be formed from any suitable material. In some implementations, the material forming the IOL insertion cartridge 200 may contain a lubricity enhancing agent.

Although FIG. 2 illustrates one implementation of an IOL insertion cartridge, other implementations may include fewer, additional, and/or a different arrangement of components. In some implementations, for example, body 210 may not include wings 217. Additionally, passage 214 may have a symmetrical bore. For example, the passage 214 may have a round or elliptical bore.

Returning to system 100, as end 122a of plunger 120 is moved toward shell 110, IOL interface 124 advances an IOL through the IOL insertion cartridge, such as IOL insertion cartridge 200. As end 122a is moved toward shell 110, second end 128b of sleeve 127 engages a portion of shell 110, as shown in FIG. 1B. As mentioned previously, this may, for example, be defined so as to occur when the IOL is entering or in the tip of an IOL insertion cartridge.

When the second end 128b of sleeve 127 engages shell 110, sleeve 127 may begin to provide force feedback to the user. As the user continues to advance end 122a toward shell 110, deformation of the sleeve 127 may provide additional force feedback. If the amount of force feedback being provided by the IOL should suddenly decrease, sleeve 127 may continue to provide force feedback, although possibly at a lower level than that of the IOL and the sleeve 127 combined. Consequently, the resistance provided by deformation of the sleeve 127 prevents a sudden advancement of the plunger 120 and, thereby, prevents the folded IOL from being rapidly introduced into the eye. Thus, the sleeve 127 aids in preventing injury to the eye. Further, the resistance provided by deformation of sleeve 127 provides for enhanced control of the IOL folding and insertion process, particularly when resistance due to folding of the IOL ceases.

Figure 3:
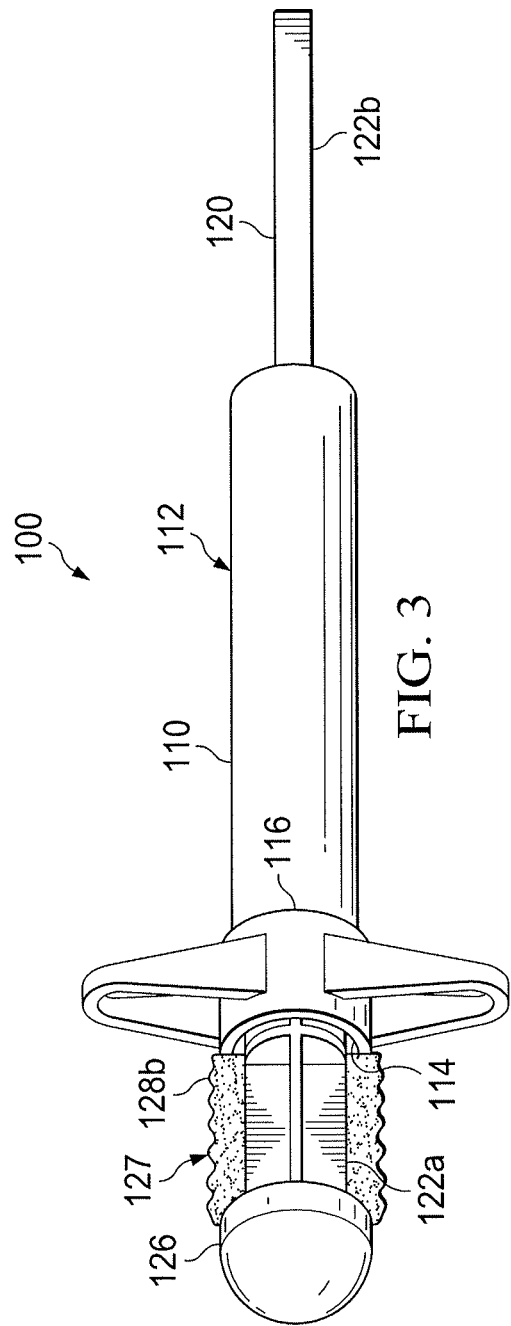
FIG. 3 is a partial cross-sectional view of the example plunger system of FIG. 1A in which a sleeve has undergone deformation.

FIG. 3 illustrates an example deformation for sleeve 127. As illustrated, first end 122a of plunger 120 has been advanced towards shell 110 beyond the point at which second end 128b engages the shell 110, which causes plunger 120 to advance further through passage 114 and moves second end 122b away from shell 110. Because of this advancement, sleeve 127 is compressed between annular ring 126 and annular ring 116. Compression of the sleeve 127 causes dimensions of the sleeve 127 to alter. For example, in the illustrated example, the compression of sleeve 127 has caused the cross-sectional width of the sleeve 127 to increase and its outer surface to wrinkle or otherwise distort.

In certain implementations, the cross-sectional size of sleeve 127 may not appreciably change due to compression. This may, for example, occur if the sleeve 127 is made of foam. Additionally, in some implementations the sleeve 127 may bulge (e.g., along its surface) or otherwise distort while being deformed by compression.

In some implementations, a reduction in the amount of force being applied to advance plunger 120 through passage 114 may cause the sleeve 127 to retain its then-current shape. Thus, the plunger 120 may remain in its current position even if a decrease in advancement force occurs, which may prevent the user from having to constantly apply a particular force to prevent the plunger 120 from retracting from shell 110. In certain implementations, the sleeve 127 may maintain its shape even if the amount of advancement force is reduced to zero. Thus, the plunger 120 may remain at the same location relative to the shell 110 after removal of the advancement force as the location occupied just prior to removal of such force. This characteristic allows the user, for example, to remove or otherwise reposition his hand relative to the plunger 120 without concern for the plunger 120 retracting from the shell 110 in the direction of arrow 131 (shown in FIG. 1A). In some implementations, the sleeve 127 may expand after a user reduces the amount of advancement force being applied. However, any such expansion may be a relatively small amount.

System 100 provides a variety of features. For example, system 100 allows an insertion system to provide force feedback as an IOL is prepared for insertion into an eye. This may assist in counteracting sudden changes in resistance of the IOL and uncontrolled advancement, which can result, and avoid improper insertion of the IOL and damage to eye tissue. Moreover, the feedback may occur automatically, with no end user actions, which can ease burden on the user.

Additionally, as opposed to devices utilizing springs to provide resistance to advancement of the plunger, system 100 can allow a user to reduce the force being applied to the plunger 120 without fear of the plunger rebounding out of or retracting from the shell. For example, a user may release or otherwise reduce an applied force to the plunger 120 in order to manipulate another instrument. In contrast, a compressed spring, by design, provides a reaction force requiring the user to continually exert an equal and opposing force to prevent an undesirable retraction of the plunger during delivery of the lens. Thus, any reduction in force causes the plunger to rebound out of or retract from the shell as a result of the force of the spring. Moreover, the sleeve 127 may provide a more glove-friendly system as compared to a spring system, which can snag and tear surgical gloves.

Furthermore, the sleeve 127 may be easy to manufacture and very reliable. IOL injection systems that use interference fits between components to influence the rate of plunger advancement can provide be very erratic in practice, and the tight dimensional tolerances require increased manufacturing costs. Moreover, tight control of manufacturing processes over time is also required in order to maintain the product dimensional specifications, further increasing manufacturing costs.

System 100 is also generally usable with pre-loaded and manually loaded IOL insertion cartridges. Moreover, the tips of the cartridges may have various shapes. For example, cartridge tips may have an oval, circular, elliptical, or any other suitable shape. Generally, a cartridge tip may have an oval, circular, or elliptical shape as these shapes are highly compatibility with the incision formed in the eye.

Although FIGS. 1A-B illustrate one implementation of a plunger system for IOL surgery, other implementations may include fewer, additional, and/or a different arrangement of components. For example, a plunger system may not include annular ring 116 or annular ring 126. In such examples, the sleeve 127 may be compressed between different features of the plunger system. As another example, body 121 may not be a cylinder. For instance, body 121 could be a cylinder. As a further example, IOL interface 124 may not be rectangular in cross section. For example, in some instances, the IOL interface may have an elliptical, oval, or any other suitable shape.

In certain implementations, sleeve 127 may be located at other areas of plunger system 100. For example, sleeve 127 could be located away from end 122a. For example, in some instances, the sleeve 127 may be located at a position toward end 122b. As another example, some or all of sleeve 127 could be located inside shell 110. In particular implementations, the sleeve 127 may be around the plunger 120 (e.g., when some or all of the deformable material is located inside the shell), but not engage the plunger 120 until it has been advanced. In some implementations, sleeve 127 may have an accordion design, and the inside of shell 110 may assist in ensuring the sleeve 127 folds in a desired manner.

In certain implementations, plunger system 100 may be designed for a single use. For example, sleeve 127 may be retained within shell 110 as plunger 120 advances so that the deformable material cannot retract.

Figure 4:
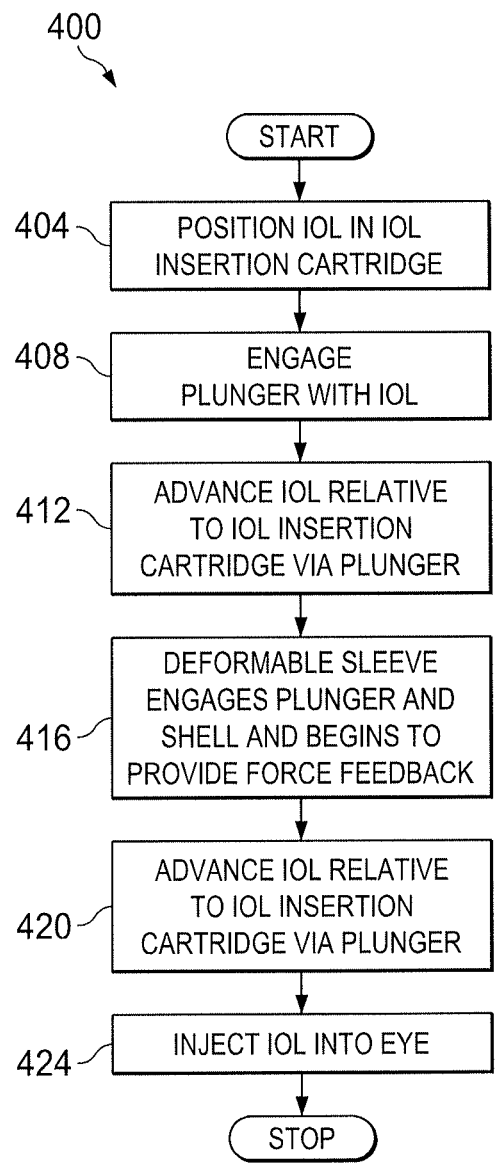
FIG. 4 is a flowchart illustrating an example process for intraocular lens surgery.

FIG. 4 illustrates an example process 400 for using a plunger system for intraocular lens surgery. Process 400 may, for instance, be performed using a plunger system similar to plunger system 100.

Process 400 includes positioning an IOL in an IOL insertion cartridge (operation 404). The IOL insertion cartridge may, for example, be similar to IOL insertion cartridge 200.

Process 400 also includes engaging a plunger of a plunger system with the IOL (operation 408). The plunger may, for example, be engaged with the IOL by advancing the tip of the plunger until it touches the IOL.

Process 400 further includes advancing the IOL relative to the IOL insertion cartridge using the plunger (operation 412). For example, the plunger may be advanced relative to the shell of the plunger system, which may move the IOL in the IOL insertion cartridge. The IOL may be folded by advancement through the IOL insertion cartridge.

As the IOL is moved relative to the IOL insertion cartridge, a deformable sleeve around the plunger may engage the plunger and the shell. As the plunger is advanced through the shell, the sleeve provides force feedback as the sleeve is compressed or otherwise deformed due to interaction with the plunger and shell (operation 416). In some instances, the deformable sleeve may be engaged with only one of the plunger or the shell at the beginning of the advancement and then brought into engagement with the other due to the advancement.

Process 400 also includes further advancing the IOL relative to the IOL insertion cartridge using the plunger (operation 420). The additional advancement may further fold the IOL and deform the sleeve, which may provide more force feedback.

Process 400 additionally includes injecting the IOL into an eye (operation 424). For example, the IOL may be injected when it reaches the end of the IOL insertion cartridge.

Although process 400 illustrates one example of a process for using a plunger system for IOL surgery, other processes for using a plunger system for IOL surgery may include fewer, additional, and or a different arrangement of operations. For example, a process may not include positioning the IOL in the IOL insertion cartridge. The IOL may, for instance, have been pre-positioned in the IOL insertion cartridge. As another example, a process may call for engaging the plunger system with the IOL insertion cartridge.

The various implementations discussed and mentioned herein have been used for illustrative purposes only. The implementations were chosen and described in order to explain the principles of the disclosure and the practical application and to allow those of ordinary skill in the art to understand the disclosure for various implementations with various modifications as are suited to the particular use contemplated. Thus, the actual physical configuration of components may vary. For example, the mentioned size(s) of components and their illustrated sizing relative to each other may vary based on application. Moreover, the shapes of one or more components may vary depending on application. Thus, the illustrative implementations should not be construed as defining the only physical size, shape, and relationship of components.

The terminology used herein is for the purpose of describing particular implementations only and is not intended to be limiting. As used herein, the singular form "a", "an", and "the" are intended to include the plural forms as well, unless the context clearly indicates otherwise. It will be further understood that the terms "comprises" and/or "comprising," when used in the this specification, specify the presence of stated features, integers, steps, operations, elements, and/or components, but do not preclude the presence or addition of one or more other features, integers, steps, operations, elements, components, and/or groups therefore.

The corresponding structure, materials, acts, and equivalents of all means or steps plus function elements in the claims below are intended to include any structure, material, or act for performing the function in combination with other claimed elements as specifically claimed. The description of the present implementations has been presented for purposes of illustration and description, but is not intended to be exhaustive or limited to the implementations in the form disclosed. Many modifications and variations will be apparent to those of ordinary skill in the art without departing from the scope and spirit of the disclosure.

A number of implementations have been described for a plunger system for intraocular lens surgery, and several others have been mentioned or suggested. Moreover, those skilled in the art will readily recognize that a variety of additions, deletions, modifications, and substitutions may be made to these implementations while still providing a plunger system for intraocular lens surgery. Thus, the scope of the protected subject matter should be judged based on the following claims, which may capture one or more concepts of one or more implementations.

The invention claimed is:

1. A system for intraocular lens surgery, the system comprising:
    a shell comprising an outer wall and an inner wall, the inner wall defining a passage through the shell;
    a plunger adapted to move within the passage, the plunger comprising:
        a first end adapted to be engaged by a user for advancing the plunger within the passage; and
        a second end comprising an intraocular lens interface; and
    a deformable sleeve disposed around the plunger, the deformable sleeve adapted to engage with the shell and the plunger to provide force feedback in response to advancement of the plunger through the passage, the force feedback being too small to cause retraction of the plunger, wherein a distal end of the deformable sleeve is spaced apart along the plunger from the second end of the plunger.

2. The system of claim 1, wherein the deformable sleeve is engaged with the plunger and moves therewith while not engaged with the shell.

3. The system of claim 2, wherein the deformable sleeve is adapted to engage with the outer wall of the shell as the plunger is moved through the passage.

4. The system of claim 2, wherein the deformable sleeve is adapted to engage with the inner wall of the shell as the plunger is moved through the passage.

5. The system of claim 1, wherein at least a portion of the deformable sleeve engages the shell, and the deformable sleeve engages with the plunger as the plunger is advanced through the passage.

6. The system of claim 5, wherein the deformable sleeve engages the inner wall of the shell.

7. The system of claim 1, wherein the deformable sleeve comprises silicone.

8. The system of claim 1, further comprising an injection cartridge comprising a portion adapted to fold the intraocular lens as it passes therethrough, wherein the deformable sleeve is adapted to begin providing force feedback when the intraocular lens is in the folding portion.

9. The system of claim 1, wherein the deformable sleeve includes at least one of: cavities, protuberances, grooves, and fold lines.

10. The system of claim 1, wherein the deformable sleeve engages an annular ring of the outer wall.

11. A system for intraocular lens surgery, the system comprising:
    a shell comprising an outer wall and an inner wall, the inner wall defining a passage through the shell;
    a plunger adapted to move within the passage, the plunger comprising:
        a first end adapted to be engaged by a user for advancing the plunger within the passage; and
        a second end comprising an intraocular lens interface; and
    a deformable sleeve disposed around the plunger, the deformable sleeve adapted to engage with the shell and the plunger to provide force feedback in response to advancement of the plunger through the passage, wherein a distal end of the deformable sleeve is spaced apart along the plunger from of the second end of the plunger; wherein the deformable sleeve is adapted to substantially maintain its shape if an applied force is removed from the plunger, the shape of the deformable sleeve being the shape at the instant the applied force is removed.

12. A method comprising:
    engaging a plunger with an intraocular lens;
    moving a first end of the plunger towards a shell to advance the intraocular lens relative to an intraocular lens insertion cartridge, the shell comprising an inner portion and an outer portion;
    engaging a deformable sleeve with the outer portion of the shell and the plunger, the deformable sleeve being spaced apart along the plunger from a second end of the plunger, the second end comprising the intraocular lens insertion cartridge, the engaged deformable sleeve providing force feedback to advancement of the plunger relative to the shell, the force feedback being too small to cause retraction of the plunger; and
    advancing the IOL relative to the IOL insertion cartridge with the deformable sleeve providing force feedback.

13. The method of claim 12, further comprising positioning the intraocular lens in the insertion cartridge.

14. The method of claim 12, further comprising injecting the intraocular lens into an eye.

15. The method of claim 12, further comprising decreasing the force applied to move the plunger towards the shell, wherein the deformable sleeve substantially maintains its shape so as not to cause the plunger to rebound away from the shell.

16. The method of claim 12, wherein compression of the deformable sleeve squeezes air out of pockets of the deformable sleeve.

17. The method of claim 12, wherein a distal end of the deformable sleeve is located away from a proximal end of the plunger.

18. A system for intraocular lens surgery, the system comprising:
    a shell comprising an outer portion with an outer wall and comprising an inner wall, the inner wall defining a passage through the shell;
    a plunger adapted to move within the passage, the plunger comprising:
        a first end adapted to be engaged by a user for advancing the plunger within the passage; and
        a second end comprising an intraocular lens interface; and
    a deformable sleeve spaced apart along the plunger from the second end of the plunger, the deformable sleeve adapted to engage with the outer portion of the shell and the plunger to provide force in response to advancement of the plunger through the passage, the force feedback being too small to cause retraction of the plunger.

19. The system of claim 18, wherein a distal end of the deformable sleeve is proximal to the second end of the plunger.

20. The system of claim 18, wherein the deformable sleeve is adapted to engage an annular ring of the outer wall of the shell.

* * * * *